United States Patent

Sasse et al.

Patent Number: 4,627,871
Date of Patent: Dec. 9, 1986

[54] HERBICIDAL 2-[4-SUBSTITUTED CARBOXYAMINO-PHENOXY (OR PHENYL MERCAPTO)]-SUBSTITUTED PYRIMIDINES

[75] Inventors: Klaus Sasse, Bergisch-Gladbach; Ludwig Eue, Leverkusen; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 737,977

[22] Filed: May 24, 1985

[30] Foreign Application Priority Data

Jun. 14, 1984 [DE] Fed. Rep. of Germany ....... 3422077

[51] Int. Cl.[4] ................... A01N 43/48; C07D 239/02
[52] U.S. Cl. ........................ 71/92; 544/316; 544/318
[58] Field of Search ............... 544/316, 318; 71/92

[56] References Cited

U.S. PATENT DOCUMENTS 3,126,271 3/1964 Thomson et al. ............... 71/92
3,250,775 5/1966 Brokke ...................... 544/315

FOREIGN PATENT DOCUMENTS 0015124 6/1983 European Pat. Off. .
2501648 7/1975 Fed. Rep. of Germany .
42-9474 5/1967 Japan .

OTHER PUBLICATIONS

Derwent Japanese 11.5.67–17.5.67, vol. 6, No. 19—9474/67.
Ishihara Sangyo Kaisha, Ltd., Chem. Abst., 94-83966j (1981) eq. JP 122763.
Ishihara Sangyo Kaisha, Ltd., Chem. Abst., 95-62252d, eq. JP 29576.
Ishihara Sangyo Kaisha, Ltd., Chem. Abst., 96-6602b, eq. JP 123970.
Johnston, Chem. Abst., 83-193095e, eq. DE 2501648.

Primary Examiner—Donald G. Daus
Assistant Examiner—Cecilia Shen
Attorney, Agent, or Firm—Sprung Horn Kramer & Woods

[57] ABSTRACT

The novel substituted carboxylic acid anilides of the formula

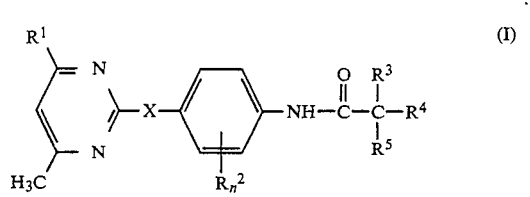

in which
X represents oxygen or sulphur,
$R^1$ represents hydrogen, halogen, alkyl with 1 to 6 carbon atoms, trifluoromethyl, optionally substituted phenyl, alkoxy with 1 to 6 carbon atoms or alkylmercapto with 1 to 6 carbon atoms,
$R^2$ represents halogen or methyl,
n represents 0, 1 or 2,
$R^3$ represents hydrogen, halogen, optionally substituted alkyl with 1 to 6 carbon atoms, optionally substituted aryl, optionally substituted aralkyl or the radicals $-OR^6$ or $-SO_m-R^6$,
wherein
$R^6$ represents optionally substituted alkyl with 1 to 6 carbon atoms or optionally substituted aryl and
m represents 0, 1 or 2, and
$R^4$ and $R^5$ independently of one another represent halogen or optionally substituted alkyl with 1 to 6 carbon atoms, or
$R^4$ and $R^5$, together with the adjacent carbon atom, represent an optionally substituted, saturated or unsaturated carbocyclic ring with 3 to 8 ring carbon atoms, are very active herbicides.

19 Claims, No Drawings

HERBICIDAL 2-[4-SUBSTITUTED CARBOXYAMINO-PHENOXY (OR PHENYL MERCAPTO)]-SUBSTITUTED PYRIMIDINES

The present invention relates to new substituted carboxylic acid anilides, to herbicidal compositions containing them, and to their use as herbicides.

It is already known that certain carboxylic acid anilides have herbicidal properties (compare R. Wegler "Chemie der Pflanzenschutz- und Schadlingsbekämpfungsmittel" ["Chemistry of Plant Protection Agents and Agents for Combating Pests"] volume 2, pages 311–314, Springer-Verlag, Berlin 1970). Thus, for example, propionic acid 3,4-dichloroanilide can be used for combating weeds. The action of this compound is good, but some weeds are not always completely affected when small amounts are applied. In addition, the selectivity also leave something to be desired in some cases.

It is furthermore known that numerous pyrimidin-2-yl ethers and thioethers are suitable as herbicides (compare Japanese Preliminary Published Application No. 9,474/1967, U.S. Spec. No. 3,126,271 and U.S. Pat. No. 3,250,775). For example, 2-phenoxy-4,6-dimethyl-pyrimidine and 2-(4-chlorobenzylmercapto)-4,6-dimethyl-pyrimidine can be used for combating weeds. However, the herbicidal potency of these substances is not always adequate.

It is also known that lower acyl derivatives of 4-pyridyloxy-(or thio) anilines have herbicidal properties (compare DE-OS (German Published Specification) No. 2,501,648, Japanese Preliminary Published Application No. 55-122,763 and Japanese Preliminary Published Application No. 56-123,970). Moreover, herbicidally active acyl derivatives of 4-pyrimidyloxy-anilines which are substituted by halogen or trifluoromethyl in the 5-position of the pryrimidyl radical but contain no substituents in positions 4 and 6 are also known (compare Japanese Preliminary Published Application No. 56-029,576). The activity of these substances, however, is always not satisfactory for practical purposes.

The present invention now provides, as new compounds, the substituted carboxylic acid anilides of the formula

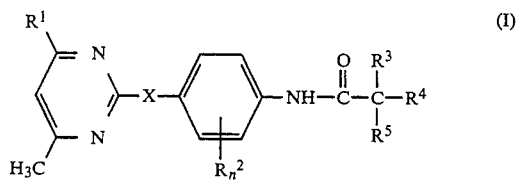

in which
X represents oxygen or sulphur,
R$^1$ represents hydrogen, halogen, alkyl with 1 to 6 carbon atoms, trifluoromethyl, optionally substituted phenyl, alkoxy with 1 to 6 carbon atoms or alkylmercapto with 1 to 6 carbon atoms,
R$^2$ represents halogen or methyl,
n represents 0, 1 or 2,
R$^3$ represents hydrogen, halogen, optionally substituted alkyl with 1 to 6 carbon atoms, optionally substituted aryl, optionally substituted aralkyl or for the radicals —OR$^6$ or —SO$_m$—R$^6$,
wherein
R$^6$ represents optionally substituted alkyl with 1 to 6 carbon atoms or optionally substituted aryl and
m represents 0, 1 or 2, and
R$^4$ and R$^5$ independently of one another represent halogen or optionally substituted alkyl with 1 to 6 carbon atoms, or
R$^4$ and R$^5$, together with the adjacent carbon atom, represent an optionally substituted, saturated or unsaturated carbocyclic ring with 3 to 8 ring carbon atoms.

The present invention also provides a process for the preparation of a substituted carboxylic acid anilide of the formula (I), in which process
(a) aniline derivatives of the formula

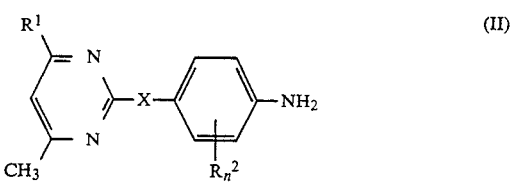

in which
R$^1$, R$^2$, X and n have the abovementioned meaning, either
(α) are reacted with acid halides of the formula

ps in which
R$^3$, R$^4$, and R$^5$ have the abovementioned meaning and
Y represents halogen,
if appropriate in the presence of a diluent and if appropriate in the presence of an acid-binding agent, or
(β) are reacted with symmetric carboxylic acid anhydrides of the formula

in which
R$^3$, R$^4$ and R$^5$ have the abovementioned meaning,
if appropriate in the presence of a diluent, or
(γ) are reacted with asymmetric acid anhydrides of the formula

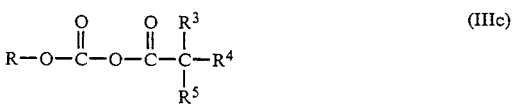

in which
R$^3$, R$^4$ and R$^5$ have the abovementioned meaning and
R represents alkyl with 1 to 4 carbon atoms or phenyl,
if appropriate in the presence of a diluent, or
(δ) are reacted with compounds of the formula

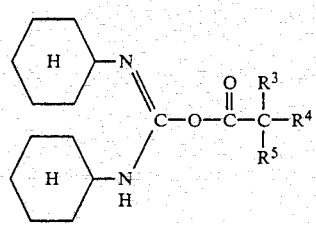

(IIId)

in which

R³, R⁴ and R⁵ have the abovementioned meaning,
if appropriate in the presence of a diluent, or (b) pyrimidine derivatives of the formula

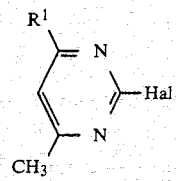

(IV)

in which

R¹ has the abovementioned meaning and

Hal represents halogen, are reacted with acyl aniline derivatives of the formula

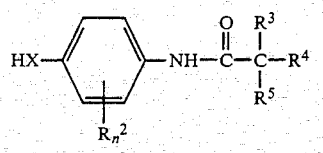

(V)

in which

Rhu 2, R³, R⁴, R⁵, x and n have the abovementioned meaning, in the presence of a diluent.

Finally, it has been found that the new substituted carboxylic acid anilides of the formula (I) are distinguished by an outstanding herbicidal activity.

Surprisingly, the substituted carboxylic acid anilides of the formula (I) according to the invention have substantially better herbicidal properties than those of the substances which are already known and which are structurally the most similar. Thus, the carboxylic acid anilides of the formula (I) according to the invention can be considerably better used for combating weeds than 2-phenoxy-4,6-dimethylpyrimidine, which is an active compound which is already known and is structurally similar and has the same type of action.

Formula (I) provides a general definition of the substituted carboxylic acid anilides according to the invention. In this formula, X represents oxygen or sulphur. The radical R¹ preferably represents hydrogen, fluorine, chlorine, bromine, straight-chain or branched alkyl with 1 to 4 carbon atoms, trifluoromethyl, phenyl which is optionally substituted by chlorine, trifluoromethyl and/or methyl, alkoxy with 1 to 4 carbon atoms or alkylmercapto with 1 to 4 carbon atoms. R² preferably represents chlorine, bromine or methyl. The index n preferably represents 0 or 1. R³ preferably represents hydrogen, fluorine, chlorine, bromine, alkyl which has 1 to 4 carbon atoms and is optionally substituted by fluorine, chlorine and/or bromine, phenyl which is optionally substituted by fluorine, chlorine, bromine, trifluoromethyl, methoxy and/or methyl, benzyl which is optionally substituted by fluorine, chlorine, bromine, trifluoromethyl, methoxy and/or methyl, or the radical —OR⁶ or —SO$_m$—R⁶, R⁶ preferably representing alkyl which has 1 to 4 carbon atoms and is optionally substituted by fluorine, chlorine and/or bromine, or phenyl which is optionally substituted by fluorine, chlorine, bromine and/or alkyl with 1 to 4 carbon atoms and the index m representing 0, 1 or 2. R⁴ and R⁵ independently of one another preferably represent fluorine, chlorine, bromine or alkyl which has 1 to 4 carbon atoms and is optionally substituted by fluorine, chlorine and/or bromine. Furthermore, R⁴ and R⁵, together with the adjacent carbon atom, also preferably represent a saturated or unsaturated carbocyclic ring which has 3 to 7 ring carbon atoms and is optionally substituted by fluorine, chlorine and/or alkyl with 1 to 4 carbon atoms.

A particularly preferred group of substances according to the invention are those substituted carboxylic acid anilides of the formula (I)

in which

X represents oxygen or sulphur,

R¹ represents hydrogen, alkyl with 1 to 4 carbon atoms, alkoxy with 1 to 4 carbon atoms or trifluoromethyl, R² represents chlorine, bromine or methyl, n represents 0 or 1, R³ represents fluorine, chlorine, bromine, alkyl which has 1 to 4 carbon atoms and is optionally substituted by fluorine and/or chlorine, phenyl which is optionally substituted by fluorine, chlorine and/or methyl, benzyl which is optionally substituted by fluorine, chlorine and/or methyl, or the radicals —OR⁶ or —SO$_m$—R⁶, wherein R⁶ represents alkyl which has 1 to 4 carbon atoms and is optionally substituted by fluorine and/or chlorine, or phenyl which is optionally substituted by fluorine, chlorine and/or alkyl with 1 to 4 carbon atoms and m represents 0, 1 or 2, and R⁴ and R⁵ independently of one another represent fluorine, chlorine or alkyl which has 1 to 4 carbon atoms and is optionally substituted by fluorine and/or chlorine, or R⁴ and R⁵, together with the adjacent carbon atom, represent a saturated or unsaturated carbocyclic ring which has 3 to 7 ring carbon atoms and is optionally substituted by fluorine, chlorine, methyl, ethyl, n-propyl, isopropyl, n-butyl, isobutyl, sec.-butyl and/or tert.-butyl.

The substances listed in the following Table 1 may be mentioned as examples of substituted carboxylic acid anilides of the formula (I).

TABLE 1

| R¹ | X | R$_n$² | R³ | R⁴ | R⁵ |
|---|---|---|---|---|---|
| H | O | H | C₂H₅ | CH₃ | CH₃ |

(I)

TABLE 1-continued

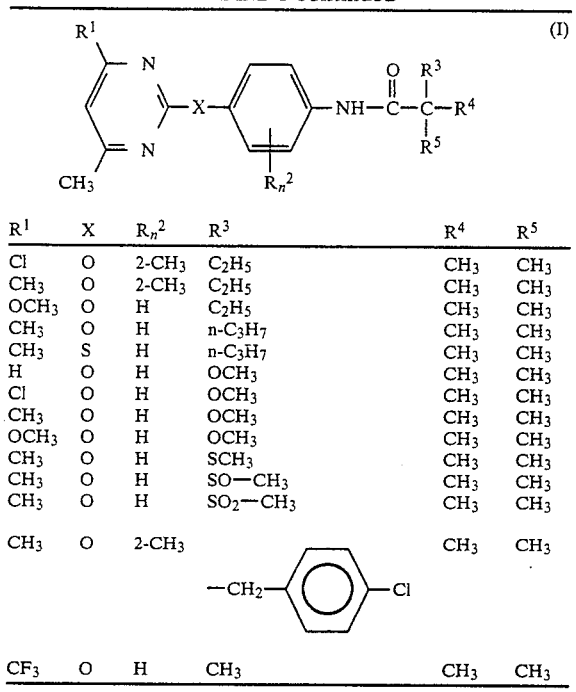

| R¹ | X | R$_n^2$ | R³ | R⁴ | R⁵ |
|---|---|---|---|---|---|
| Cl | O | 2-CH₃ | C₂H₅ | CH₃ | CH₃ |
| CH₃ | O | 2-CH₃ | C₂H₅ | CH₃ | CH₃ |
| OCH₃ | O | H | C₂H₅ | CH₃ | CH₃ |
| CH₃ | O | H | n-C₃H₇ | CH₃ | CH₃ |
| CH₃ | S | H | n-C₃H₇ | CH₃ | CH₃ |
| H | O | H | OCH₃ | CH₃ | CH₃ |
| Cl | O | H | OCH₃ | CH₃ | CH₃ |
| CH₃ | O | H | OCH₃ | CH₃ | CH₃ |
| OCH₃ | O | H | OCH₃ | CH₃ | CH₃ |
| CH₃ | O | H | SCH₃ | CH₃ | CH₃ |
| CH₃ | O | H | SO—CH₃ | CH₃ | CH₃ |
| CH₃ | O | H | SO₂—CH₃ | CH₃ | CH₃ |
| CH₃ | O | 2-CH₃ | —CH₂—C₆H₄—Cl | CH₃ | CH₃ |
| CF₃ | O | H | CH₃ | CH₃ | CH₃ |

If 4-(4,6-dimethyl-pyrimid-2-yloxy)-aniline and pivalyl chloride are used as starting substances, the course of process (a, variant α) according to the invention can be represented by the following equation:

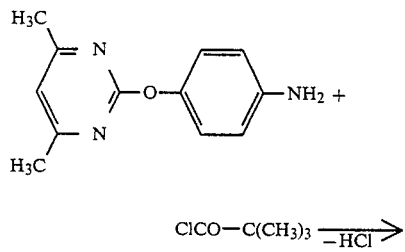

ClCO—C(CH₃)₃ $\xrightarrow{-HCl}$

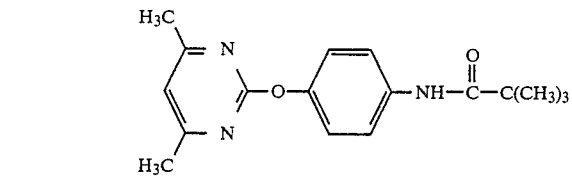

If 4-(4-methyl-pyrimid-2-ylmercapto)-aniline and isobutyric anhydride are used as the starting substances, the course of process (a, variant β) according to the invention can be represented by the following equation:

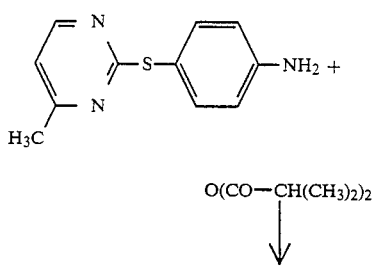

O(CO—CH(CH₃)₂)₂

↓

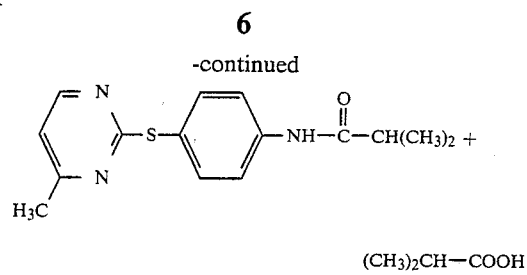

(CH₃)₂CH—COOH

If 4-(4,6-dimethyl-pyrimid-2-ylmercapto)-aniline and α-methoxy-isobutyric acid-carbonic acid ether ester anyhydride are used as starting substances, the course of process (a, variant γ) according to the invention can be represented by the following equation:

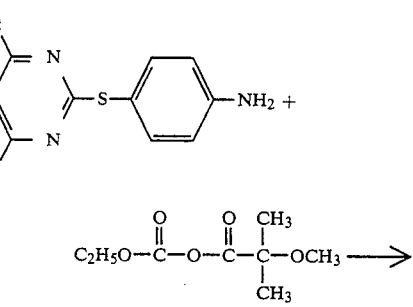

$$C_2H_5O-\overset{O}{\overset{\|}{C}}-O-\overset{O}{\overset{\|}{C}}-\overset{CH_3}{\underset{CH_3}{\overset{|}{C}}}-OCH_3 \longrightarrow$$

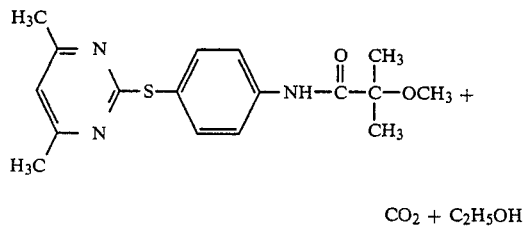

CO₂ + C₂H₅OH

If 4-(4,6-dimethyl-pyrimid-2-yloxy)-aniline and O-pivalyloxy-dicyclohexyl-isourea are used as starting substances, the course of process (a, variant δ) according to the invention can be represented by the following equation:

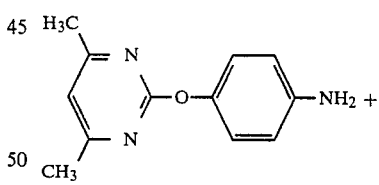

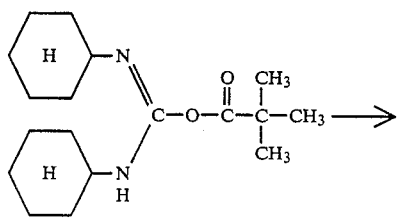

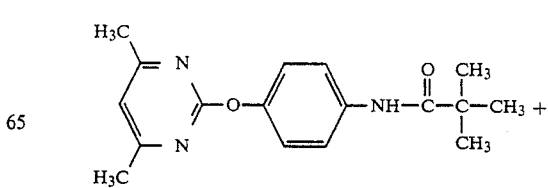

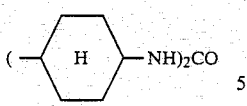

If 2-chloro-4,6-dimethyl-pyrimidine and 4-pivalylamino-phenol are used as starting substances, the course of process (b) according to the invention can be represented by the following equation:

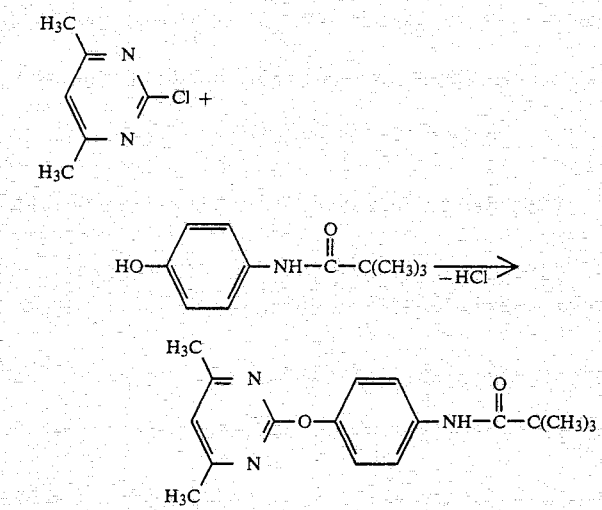

Formula (II) provides a general definition of the aniline derivatives required as starting substances in process (a) according to the invention. In this formula, $R^1$, $R^2$, X and n preferably have those meanings which have already been mentioned as preferred in connection with the description of the substances of the formula (I) for these radicals and this index.

Some of the aniline derivatives of the formula (II) are known. They can be prepared by a process in which:

(c) pyrimidine derivatives of the formula

(IV)

in which
$R^1$ and Hal have the abovementioned meaning,
are reacted with 4-amino-(thio)-phenols of the formula

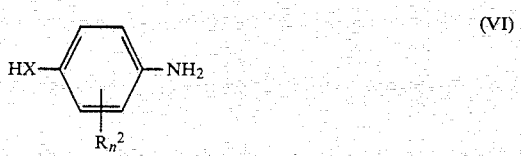

(VI)

in which
$R^{2'}$, X and n have the abovementioned meaning,
in the presence of an acid-binding agent and, if appropriate, in the presence of a diluent, or (d) 2-(4-nitro-(thio)-phenoxy)-pyrimidine derivatives of the formula

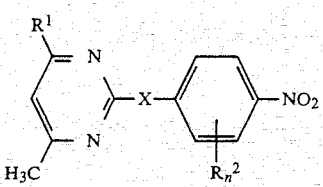

(VII)

in which
$R^1$, $R^2$, X and n have the abovementioned meaning,
are reduced by customary methods, if appropriate in the presence of a diluent.

Formula (IV) provides a definition of the pyrimidine derivatives required as starting substances in the above process (c). In this formula, $R^1$ preferably has those meanings which have already been mentioned as preferred for this radical in connection with the description of the substances of the formula (I) according to the invention. Hal preferably represents fluorine, chlorine or bromine.

Examples which may be mentioned for pyrimidine derivatives of the formula (IV) are:
2-chloro-4-methyl-pyrimidine,
2-bromo-4-methyl-pyrimidine,
2,4-dichloro-6-methyl-pyrimidine,
2-chloro-4-methoxy-6-methyl-pyrimidine,
2-chloro-4-methylmercapto-6-methyl-pyrimidine,
2-chloro-4,6-dimethyl-pyrimidine,
2-fluoro-4,6-dimethyl-pyrimidine,
2-chloro-4-methyl-6-propyl-pyrimidine,
2-chloro-4-methyl-6-isopropyl-pyrimidine,
2-chloro-4-methyl-6-trifluoromethyl-pyrimidine,
2-chloro-4-methyl-6-phenyl-pyrimidine,
2-chloro-4-methyl-6-(4-chloro-phenyl)-pyrimidine,
2-chloro-4-methyl-6-(4-methyl-phenyl)-pyrimidine,
2-chloro-4-methyl-6-(3-trifluoromethyl-phenyl)-pyrimidine The pyrimidine derivatives of the formula (IV) are known or they can be prepared in a simple manner by methods which are known in principle. Thus, pyrimidine derivatives of the formula (IV) are obtained, for example, by reacting 2-hydroxy-pyrimidine derivatives (dihydro-pyrimid-2-one derivatives) with inorganic acid halides, such as, for example, phosphorous oxychloride or phosphorous pentachloride, or by reacting corresponding 2-amino-pyrimidine derivatives with nitrous acid in the presence of hydrogen halide acids.

Formula (VI) provides a definition of the 4-amino-(thio)-phenols furthermore required as starting substances in process (c). In this formula, $R^2$, X and n preferably have those meanings which have already been mentioned as preferred for these radicals and for this index in connection with the description of the substances of the formula (I) according to the invention.

Examples which may be mentioned of 4-amino-(thio)-phenols of the formula (VI) are:
4-amino-phenol,
2-chloro-4-amino-phenol,
3-chloro-4-amino-phenol,
2,5-dichloro-4-amino-phenol,
2,6-dichloro-4-amino-phenol,
2-methyl-4-amino-phenol,
3-methyl-4-amino-phenol,
2-chloro-5-methyl-4-amino-phenol,
4-amino-thiophenol,
2-chloro-4-amino-thiophenol, 3-chloro-4-amino-thiophenol,
2-methyl-4-amino-thiophenol, and
3-methyl-4-amino-thiophenol.

The 4-amino-(thio)-phenols of the formula (VI) are known or can be prepared in a simple manner by methods which are known in principle.

Acid-binding agents which can be used in carrying out process (c) are all the acid acceptors which can usually be employed for such reactions. Agents which can preferably be used are alkali metal and alkaline earth metal oxides, hydroxides and carbonates, such as sodium hydroxide, potassium hydroxide, calcium oxide, sodium carbonate and potassium carbonate, and furthermore alkali earth metal alcoholates, amides and hydrides, such as, for example, sodium methylate, sodium ethylate, potassium tert.-butylate, sodium amide and sodium hydride.

Diluents which can be used in carrying out process (c) are all the usual inert organic solvents. Solvents which can preferably be used are hydrocarbons, such as benzine, toluene and xylene, and furthermore, ethers, such as dioxane, glycol dimethyl ether and diglycol dimethyl ether, and in addition nitriles, such as acetonitrile and also strongly polar solvents, such as dimethylsulphoxide, sulpholane and dimethylformamide.

The reaction temperatures can be varied within a substantial range in carrying out process (c). In general, the reaction is carried out at temperatures between 0° C. and 200° C., preferably between 50° C. and 150° C.

The reaction according to process (c) is carried out in general under normal pressure.

The starting substances of the formulae (IV) and (VI) are in general reacted in approximately equimolar amounts for carrying out process (c). However, it is also possible to employ one or other of the components in a large excess. Working up is carried out by customary methods.

Formula (VII) provides a definition of the 2-(4-nitro-(thio)-phenoxy)-pyrimidine derivatives required as starting substances in process (d). In this formula, $R^1$, $R^2$, X and n preferably have those meanings which have already been mentioned as preferred for these radicals and for this index in connection with the description of the substances of the formula (I) according to the invention.

The compounds of the formula (VII) are known or they can be prepared in a simple manner by methods which are known in principle. Thus, compounds of the formula (VII) are obtained, for example, by a process in which pyrimidine derivatives of the formula

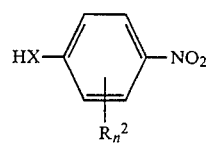

(IV)

in which
$R^1$ and Hal have the abovementioned meaning,
are reacted with 4-nitro-(thio)-phenols of the formula

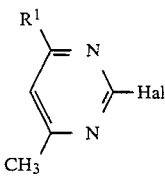

(IX)

in which
$R^2$, X and n have the abovementioned meaning,
in the presence of an acid-binding agent and if appropriate in the presence of a diluent, at temperatures between 0° C. and 200° C., preferably between 50° C. and 150° C. Possible cid-binding agents and diluents here are preferably those substances which have already been mentioned as acid acceptors and solvents which can preferably be used in connection with process (c). Possible reducing agents in process (d) are all those substances which are usually employed for reduction of aromatic nitro compounds. Elemental metals, such as iron, zinc and tin, and furthermore metal compounds in lower valency stages, such as iron(II) and tin(II) salts, and also non-metallic elements in lower valency stages, such as, for example salts of hydrogen sulphide, alkali metal sulphites and alkali metal dithionites, can preferably be used. Moreover, the reduction can also be carried out by catalytic hydrogenation with hydrogen in the presence of a catalyst, such as, for example, Raney nickel.

Possible diluents in process (d) are all the usual organic solvents which are suitable for such reductions. The reagent temperatures can be varied within a substantial range. They correspond to the temperatures which are used for analogous reactions.

The reduction according to process (d) is carried out and the reaction mixture is worked up by customary methods.

Formua (IIIa) provides an unambiguous definition of the acid halides required as reaction components in process (a, variant α) according to the invention. In this formula, $R^3$, $R^4$ and $R^5$ preferably have those meanings which have already been mentioned as preferred for these radicals in connection with the description of the substances of the formula (I) according to the invention. Y preferably represents fluorine, chlorine or bromine.

Examples which may be mentioned of acid halides of the formula (IIIa) are the chlorides of the following acids:
trichloroacetic acid,
trifluoroacetic acid,
α,α-dichloropropionic acid,
isobutyric acid,
α-chloro-isobutyric acid,
α-bromo-isobutyric acid,
α-methoxy-isobutyric acid,
α-phenoxy,-isobutyric acid,
α-(4-chloro-phenoxy)-isobutyric acid,
α-(2-methyl-4-chloro-phenoxy)-isobutyric acid,
α-methylmercapto-isobutyric acid,
α-methylsulphonyl-isobutyric acid,
α-methyl-butyric acid,
pivalic acid,
β-fluoro-pivalic acid,
β-chloro-pivalic acid,
β,β'-difluoro-pivalic acid,
β,β'-dichloro-pivalic acid,
β,β'β''-trifluoro-pivalic acid,
β,β'β''-trichloro-pivalic acid,
α,α-dimethyl-valeric acid, α-methyl-α-ethyl-butyric acid,
α,α-dimethyl-phenyl acetic acid,
α,α-dimethyl-(4-chloro-phenyl)-acetic acid,
α,α-dimethyl-(3,4-dichloro-phenyl)-acetic acid,
α,α-dimethyl-(3-trifluoromethyl-phenyl)-acetic acid,
α-benzyl-isobutyric acid,
α-(4-chloro-benzyl)-isobutyric acid,
α-(4-methoxy-benzyl)-isobutyric acid,
cyclopropane-carboxylic acid,
1-methyl-cyclopropane-carboxylic acid,
2,2-dichloro-1-methyl-cyclopropane-carboxylic acid,
cyclopentane carboxylic acid,
1-methyl-cyclopentane-carboxylic acid,
cyclohexane-carboxylic acid,
1-methyl-cyclohexane-carboxylic acid,
and
1-methyl-4-isopropyl-cyclohexane-carboxylic acid.

The acid halides of the formula (IIIa) are known, or they can be prepared in a simple manner by methods which are known in principle.

Possible acid-binding agents in the reaction in process (a, variant α) according to the invention are all the acid acceptors which can usually be employed. Agents which can preferably be used are tertiary amines, such as triethylamine, pyridine and N,N-dimethyl-aniline, and furthermore alkaline earth metal oxides, such as magnesium oxide and calcium oxide, and also alkali metal carbonates and alkaline earth metal carbonates, such as sodium carbonate, potassium carbonate and calcium carbonate. It is also possible simultaneously to use the particular aniline derivatives of the formula (II) as the acid-binding agent. In this case, the aniline compound in question must then be present in at least an amount such that the hydrogen halide liberated can be bonded.

Diluents which can be employed in process (a, variant α) according to the invention are all the solvents which are inert towards acid halides. Solvents which can preferably be used are hydrocarbons, such as benzine, benzene, toluene, xylene and tetraline, and furthermore halogenohydrocarbons, such as methylene chloride, chloroform, carbon tetrachloride, chlorobenzene and o-dichlorobenzene, and also ketones, such as acetone and methyl isopropyl ketone, and furthermore ethers, such as diethyl ether, tetrahydrofuran and dioxane, and moreover carboxylic acid esters, such as ethyl acetate, and also strongly polar solvents, such as dimethylsulphoxide and sulpholane. If the stability of the acid halide to hydrolysis permits, the reaction can also be carried out in the presence of water.

The reaction temperatures can be varied within a substantial range in carrying out process (a, variant α) according to the invention. If the reaction is carried out without a solvent or acid-binding agent, a procedure is in general followed in which the components are initially allowed to react at temperatures between −20° C. and +20° C. and the reaction mixture is then heated to temperatures between 70° and 200° C. If the reaction is carried out in the presence of a diluent and an acid-binding agent, the reaction temperatures are in general between −20° C. and +100° C., preferably between 0° C. and 50° C.

Process (a, variant α) according to the invention is in general carried out under normal pressure.

The starting substances of the formulae (II) and (IIIa) are in general used in approximately equivalent amounts in carrying out process (a, variant α) according to the invention. However, it is also possible to employ one or other of the components in a larger excess. Working up is then carried out by customary methods. In general, a procedure is followed in which precipitated salts are removed and the reaction mixture which remains is concentrated by stripping off the diluent. If the reaction is carried out in the presence of water or water-miscible solvents, a procedure can also be followed in which the reaction mixture is diluted with water, the resulting mixture is filtered with suction or extracted with an organic solvent of low water-miscibility, the organic phase is washed and concentrated and the residue which remains is subjected to customary purification processes, if appropriate.

Formula (IIIb) provides an unambiguous definition of the symmetric carboxylic acid anhydrides required as reaction components in process (a, variant β) according to the invention. In this formula, $R^3$, $R^4$ and $R^5$ preferably have those meanings which have already been mentioned as preferred for these radicals in connectin with the description of the substances of the formula (I) according to the invention.

The symmetric carboxylic acid anhydrides of the formula (IIIb) are known or can be prepared in a simple manner by methods which are known in principle.

Diluents which can be used in carrying out process (a, variant β) according to the invention are preferably those diluents which can also possibly be used in process (a, variant α). In addition, a carboxylic acid anhydride of the formula (IIIb) employed in excess can simultaneously function as the diluent.

The reaction temperatures can also be varied within a substantial range in process (a, variant β) according to the invention. In general, the reaction is carried out at temperatures between −20° C. and +150° C., preferably between 0° and 100° C.

Process (a, variant β) according to the invention is in general carried out under normal pressure.

The starting substances of the formulae (II) and (IIIb) are in general used in approximately equivalent amounts in carrying out process (a, variant β) according to the invention. However, it is also possible to employ a larger excess of the carboxylic acid anhydride. Working up is carried out by customary methods.

In general, a procedure is followed in which diluents and carboxylic acid anhydride present in excess, as well as the carboxylic acid formed, are removed by distillation or by washing with an organic solvent or with water.

Formula (IIIc) provides an unambiguous definition of the asymmetric acid anhydrides required as reaction components in process (a, variant γ) according to the invention. In this formula, $R^3$, $R^4$ and $R^5$ preferably have those meanings which have already been mentioned as preferred for these radicals in connection with the description of the substances of the formula (I) according to the invention. R preferably represents alkyl with 1 or 2 carbon atoms or phenyl.

The asymmetric acid anhydrides of the formula (IIIc) are known or can be prepared in a simple manner by methods which are known in principle. Thus, compounds of the formula (IIIc) are obtained by a process in which carboxylic acids of the formula

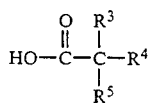

in which
R³, R⁴ and R⁵ have the abovementioned meaning,
are reacted with carbonic acid ester-chlorides of the formula

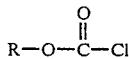

in which
R has the abovementioned meaning,
in the presence of a diluent, such as, for example, methylene chloride, and in the presence of an acid-binding agent, such as, for example, triethylamine, at temperatures between −20° C. and +100° C., preferably between 0° and 50° C. The asymmetric acid anhydrides of the formula (IIIc) are in general not isolated in the pure form but are further used in the form in which they are obtained, if appropriate after prior removal of diluent and/or salts.

Diluents which can be used in carrying out process (a, variant γ) according to the invention are preferably those diluents which can also preferably be used in process (a, variant α). Furthermore, acid anhydrides of the formula (IIIc) employed in excess can simultaneously function as the diluent.

The reaction temperatures can also be varied within a substantial range in process (a, variant γ) according to the invention. The reaction is in general carried out at temperatures between −20° C. and +150° C., preferably between 0° and 100° C.

Process (a, variant γ) according to the invention is in general carried out under normal pressure.

The starting substances of the formulae (II) and (IIIc) are in general used in approximately equivalent amounts in carrying out process (a, variant γ) according to the invention. However, it is also possible to employ the acid anhydride in a larger excess. Working up is carried out by customary methods.

Formula (IIId) provides an unambiguous definition of the compounds required as reaction components in process (a, variant δ) according to the invention. In this formula, R³, R⁴, and R⁵ preferably have those meanings which have already been mentioned as preferred for these radicals in connection with the description of the substances of the formula (I) according to the invention.

The compounds of the formula (IIId) are known or can be prepared in a simple manner by processes which are known in principle. Thus, compounds of the formula (IIId) are obtained by a process in which carboxylic acids of the formula

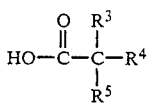

in which
R³, R⁴, and R⁵ have the abovementioned meaning,
are reacted with dicyclohexylcarbodiimide of the formula

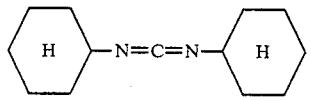

Diluents which can be used in carrying out process (a, variant δ) according to the inventin are preferably those diluents which can also preferably be used in process (a, variant α).

The reaction temperatures can also be varied within a substantial range in process (a, variantδ) according to the invention. The reaction is in general carried out at temperatures between −20° C. and +150° C., preferably between 0° and 100° C.

Process (a, variant δ) according to the invention is in general carried out under normal pressure.

The starting substances of the formulae (II) and (IIId) are in general used in approximately equivalent amounts in carrying out process (a, variant δ) according to the invention. Working up is carried out by customary methods.

The pyrimidine derivatives required as starting substances in process (b) according to the invention have already been dealt with in connection with the description of process (c).

Formula (V) provides an unambiguous definition of the acylaniline derivatives furthermore required as starting substances in process (b) according to the invention. In this formula, R², R³, R⁴, R⁵, X and n preferably have those meanings which have already been mentioned as preferred for these radicals and for this index in connection with the description of the substances of the formula (I).

The compounds of the formula (V) are known or they can be prepared in a simple manner by methods which are known in principle. Thus, acylaniline derivatives of the formula (V) are obtained, for example, by a process in which 4-amino-(thio)-phenols of the formula

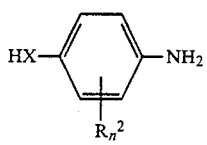

in which
R², X and n have the abovementioned meaning,
are reacted with acid halides of the formula

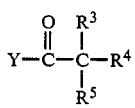

in which
R³, R⁴, R⁵ and Y have the abovementioned meaning, if appropriate in the presence of a diluent and if appropriate in the presence of an acid-binding agent. The reaction conditions here correspond to those which are also used in carrying out process (a, variant α).

Acid-binding agents which can be used in carrying out process (b) according to the invention are all the customary acid acceptors. Agents which can preferably be used are alkali metal and alkaline earth metal oxides, hydroxides and carbonates, such as sodium hydroxide, potassium hydroxide, magnesium oxide, calcium oxide, sodium carbonate, potassium carbonate and calcium carbonate, and furthermore alkali metal and alkaline earth metal amides and hydrides, such as sodium amide, sodium hydride and calcium hydride, and moreover, also alkali metal alcoholates, such as sodium methylate, sodium ethylate and potassium tert.-butylate.

Diluents which can be employed in process (b) according to the invention are all the customary inert organic solvents. Solvents which can preferably be used are hydrocarbons, such as toluene and xylene, and furthermore ethers, such as dibutyl ether, tetrahydrofuran, dioxane, glycoldimethyl ether and diglycoldimethyl ether, and also nitriles, such as acetonitrile and proprionitrile, and furthermore polar solvents, such as nitrobenzene, dimethylsulphoxide, sulfolane, dimethylformamide and N-methyl-pyrrolidone.

The reaction temperatures can be varied within a substantial range in carrying out process (b) according to the invention. In general, the reaction is carried out at temperatures between 0° and 200° C., preferably between 50° and 150° C.

Process (b) according to the invention is in general carried out under normal pressure.

In carrying out process (b) according to the invention, the reactin components of the formulae (IV) and (V) are in general employed in approximately equimolar amounts. However, it is also possible to use one or other of the components in a larger excess. In addition, an equimolar amount of acid-binding agent is in general also employed. However, it may also be advantageous to add the acid-binding agents in an excess of up to one mole. Specifically, a procedure is in general followed in which the acid-binding agent is added to a mixture of the reaction components in a suitable diluent. However, it is also possible to follow a procedure in which a salt is first produced from the acyl aniline derivative of the formula (V) and the acid-binding agent and this is then reacted with a pyrimidine derivative of the formula (IV). It is furthermore also possible initially to prepare a salt separately from the acyl aniline derivative of the formula (V) with an acid-binding agent and then to isolate this salt and subsequently to react it with a pyrimidine derivative of the formula (IV) in the presence of a suitable diluent, without further addition of an acid-binding agent. Working up is in each case carried out by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera:
Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Amrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera:
Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera:
Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera:
Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are particularly suitable for selective combating of monocotyledon and dicotyledon weeds in monocotyledon cultures, such as, for example, maize and cereals.

The active compounds according to the invention also exhibit a powerful microbicidal action and can be used in practice for combating undesirable microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good tolerance by plants of the active compounds in the concentrations necessary for combating plant diseases allows treatment of above-ground parts of plants, of vegetative propagation of stock and seed, and of the soil.

The active compounds according to the invention can be particularly advantageously used for combating Pyricularia oryzae in rice, again Botrytis and for combating bean rust.

The substances according to the invention are furthermore also distinguished by an insecticidal activity. They have a good root systemic activity.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethyl-ethyl)-3-methylthio-1,2,4-triazin-5(4H)-one, 4-amino-6-(1,1-dimethyl-ethyl)-;b 3-ethylthio-1,2,4-triazin-5(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5(4H)-one, 2-chloro-4-ethylamino-6-isopropyl-amino-1,3,5-triazine, the R-enantiomer of (trimethylsilyl)-methyl 2-[4-(3,5-dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichloropohenoxy)-propionic acid, 4-chloro-2-methylphenoxy-acetic acid, 2-(2-methyl-4-chloro-phenoxy)-propionic acid, 3,5-diiodo-4-hydroxy-benzonitrile, 3,5-dibromo-4-hydroxy-benzonitrile and diphenyl ethers and phenylpyridazines, such as, for example, pyridates. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

When used as herbicides, the active compounds according to the invention can be applied either before or after emergence of the plants. They can also be incorporated into the soil before sowing.

The amount of active compound applied when the substances according to the invention are used as herbicides can vary within a substantial range. It depends essentially on the nature of the desired effect. In general, the amounts used are between 0.01 and 10 kg of active compound per hectare of soil surface, preferably between 0.05 and 5 kg per ha.

When the substances according to the inventon are used as fungicides, the amount applied can also be varied within a substantial range, depending on the nature of the application. Thus, for the treatment of parts of plants, the active compound concentrations in the use forms are in general between 1 and 0.0001% by weight, preferably between 0.5 and 0.001% by weight. In the treatment of seed, amounts of active compond of 0.001 to 50 g per kg of seed, preferably 0.01 to 10 g are in general required. In the treatment of soil, active compound concentrations of 0.00001 to 0.1% by weight, preferably 0.0001 to 0.02%, are required at the place of action.

The present invention also provides a herbicidal composition containing as active ingredient a compound of the formula (I) according to the present invention in admixture with a solid diluent or carrier or in admixture with a liquid diluent or carrier containing a surface-active agent.

The present invention also provides a method of combating weeds which comprises applying to the weeds, or to a habitat thereof, a compond of the formula (I) according to the present invention alone or in the form of a composition containing as active ingredient a compound of the formula (I) according to the present invention in admixture with a diluent or carrier.

The preparation and use of the substances according to the invention can be seen from the examples which follow.

PREPARATION EXAMPLES

Example 1

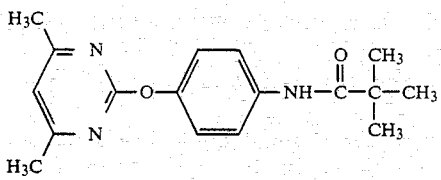
(I-1)

(Process a)

21.5 g (0.1 mole) of 2-(4-amino-phenoy)-4,6-dimethyl-pyrimidine were dissolved in 150 ml of tetrahydrofuran. 10.1 (0.1 mole) of triethylamine were added, and 12 g (0.1 mole) of pivalyl chloride were then added dropwise at a temperature of 10° to 15° C., with stirring. The mixture was subsequently stirred at room temperature for 2 hours. It was then worked up by a procedure in which the solid product precipitated was filtered off with suction and the filtrate was evaporated under reduced pressure. 27.5 g (92% of theory) of 2-(4-pivaloylamino-phenoxy)-4,6-dimethylpyrimidine remained in the form of a solid product.

Melting point: 190°–191° C. (after recrystallisation from ethyl acetate)

Example 2

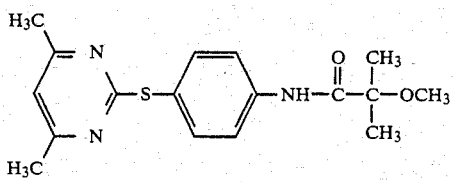
(I-2)

11.8 g (0.1 mole) of α-methoxy-isobutyric acid were dissolved in 150 ml of tetrahydrofuran, and 10.1 g (0.1 mole) of triethylamine were added. 10.85 g (0.1 mole) of carbonic acid ethyl ester-chloride were added dropwise at 10°–15° C., with stirring. The mixture was subsequently stirred at room temperature for 2 hours and 23.1 g (0.1 mole) of 2-(4-aminophenylmercapto)-4,6-dimethyl-pyrimidine were then added in portions. The mixture was subsequently stirred at room temperature for 1 hour and boiled under reflux for a further 2 hours. The reaction mixture was cooled and then stirred into one liter of water rendered slightly acid with hydrochloric acid. The crystals precipitated were filtered off with suction, washed with water and dried in air. 27.4 g (83% of theory) of 2-(4-(α-methoxy-isobutyrylamino)-phenylmercapto)-4,6-dimethyl-pyrimidine were obtained.

Melting point: 123°–125° C. (after recrystallisation from cleaner's naphtha).

Example 3

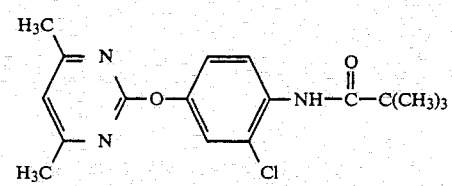
(I-3)

(Process b)

22.8 g (0.1 mole) of 3-chloro-4-pivaloylamino-phenol were dissolved in 150 ml of dimethylsulphoxide. 5.6 g (0.1 mole) of powdered potassium hydroxide were added in portions at room temperature, with stirring. The mixture was subsequently stirred at room temperature for 30 minutes and 14.25 g (0.1 mole) of 2-chloro-4,6-dimethyl-pyrimidine were then added in portions. The mixture was heated to 120° C. in the course of 1 hour and subsequently stirred at this temperature for a further 5 hours. The mixture was then cooled and poured into one liter of water. The crystals were filtered off with suction and dried in air. 25.5 g (76.5% of theory) of 2-(3-chloro-4-pivaloylamino-phenoxy)-4,6-dimethylpyrimidine were obtained.

Melting point: 83°–85° C.

The substances of the formula (I) listed by way of their formulae in the following table were also prepared by the methods described in the preceding examples and in the description.

TABLE 2

| Example No. | $R^1$ | X | $R^2$ | $R^3$ | $R^4$ | $R^5$ | melting point/(°C.) |
|---|---|---|---|---|---|---|---|
| 4 | H | O | H | $CH_3$ | $CH_3$ | $CH_3$ | 161–163 |
| 5 | H | O | H | $CH_2F$ | $CH_3$ | $CH_3$ | 132–134 |
| 6 | H | O | H | $CH_2Cl$ | $CH_3$ | $CH_3$ | 148–150 |
| 7 | H | O | H | $CH_2F$ | $CH_2F$ | $CH_2F$ | 127–129 |
| 8 | H | S | H | $CH_3$ | $CH_3$ | $CH_3$ | 150–152 |
| 9 | H | S | H | $CH_2Cl$ | $CH_3$ | $CH_3$ | 120–121 |
| 10 | H | S | H | $CH_3$ | | $-(CH_2)_4-$ | 119–121 |
| 11 | Cl | O | H | $CH_3$ | $CH_3$ | $CH_3$ | 179–181 |
| 12 | $OCH_3$ | O | H | $CH_3$ | $CH_3$ | $CH_3$ | 164–166 |
| 13 | $CH_3$ | O | H | H | $CH_3$ | $CH_3$ | 163–165 |
| 14 | $CH_3$ | O | H | H | $CH_3$ | $C_2H_5$ | 142–144 |
| 15 | $CH_3$ | O | H | H | | $-(CH_2)_5-$ | 204–206 |
| 16 | $CH_3$ | O | H | Cl | Cl | Cl | 194–196 |
| 17 | $CH_3$ | O | H | Br | $CH_3$ | $CH_3$ | 168–170 |
| 18 | $CH_3$ | O | H | $OCH_3$ | $CH_3$ | $CH_3$ | 132–134 |
| 19 | $CH_3$ | O | H | $CH_2F$ | $CH_3$ | $CH_3$ | 164–166 |

TABLE 2-continued

Structure (I): pyrimidine (with $R^1$, $N$, $N$, $H_3C$) — $X$ — phenyl (with $R^2_n$) — $NH-C(=O)-C(R^3)(R^4)(R^5)$

| Example No. | $R^1$ | X | $R^2$ | $R^3$ | $R^4$ | $R^5$ | melting point/(°C.) |
|---|---|---|---|---|---|---|---|
| 20 | $CH_3$ | O | H | $CH_2Cl$ | $CH_3$ | $CH_3$ | 168–170 |
| 21 | $CH_3$ | O | H | $CH_2F$ | $CH_2F$ | $CH_3$ | 166 |
| 22 | $CH_3$ | O | H | $CH_2Cl$ | $CH_2Cl$ | $CH_3$ | 181–182 |
| 23 | $CH_3$ | O | H | $CH_2F$ | $CH_2F$ | $CH_2F$ | 166–168 |
| 24 | $CH_3$ | O | H | $CH_2Cl$ | $CH_2Cl$ | $CH_2Cl$ | 101–103 |
| 25 | $CH_3$ | O | H | $C_3H_7$ | $CH_3$ | $CH_3$ | 138–140 |
| 26 | $CH_3$ | O | H | $C_2H_5$ | $C_2H_5$ | $CH_3$ | 158–160 |
| 27 | $CH_3$ | O | H | 4-chlorophenyl | $CH_3$ | $CH_3$ | 150–152 |
| 28 | $CH_3$ | O | H | benzyl ($CH_2$-phenyl) | $CH_3$ | $CH_3$ | 134–136 |
| 29 | $CH_3$ | O | H | $CH_3$ | $-CH_2-CH_2-$ | | 203–205 |
| 30 | $CH_3$ | O | H | $CH_3$ | $-CH_2-CCl_2-$ | | 154–156 |
| 31 | $CH_3$ | O | H | $CH_3$ | $-(CH_2)_4-$ | | 140–142 |
| 32 | $CH_3$ | O | H | $CH_3$ | $-(CH_2)_5-$ | | 139–140 |
| 33 | $CH_3$ | O | H | $CH_3$ | $-(CH_2)_2-CH[CH(CH_3)_2]-(CH_2)_2-$ | | 128–130 |
| 34 | $CH_3$ | O | 3-Cl | $CH_3$ | $CH_3$ | $CH_3$ | 205–207 |
| 35 | $CH_3$ | O | 3-Cl | $CH_2Cl$ | $CH_3$ | $CH_3$ | 182–184 |
| 36 | $CH_3$ | O | 3-Cl | $CH_2F$ | $CH_2F$ | $CH_3$ | 178–180 |
| 37 | $CH_3$ | O | 3,5-$Cl_2$ | $CH_3$ | $CH_3$ | $CH_3$ | 250–252 |
| 38 | $CH_3$ | O | 2-$CH_3$ | $CH_3$ | $CH_3$ | $CH_3$ | 164–166 |
| 39 | $CH_3$ | O | 3-$CH_3$ | $CH_3$ | $CH_3$ | $CH_3$ | 183–185 |
| 40 | $CH_3$ | S | H | Cl | Cl | Cl | 182–184 |
| 41 | $CH_3$ | S | H | Br | $CH_3$ | $CH_3$ | 160–162 |
| 42 | $CH_3$ | S | H | $SCH_3$ | $CH_3$ | $CH_3$ | |
| 43 | $CH_3$ | S | H | phenoxy (O-phenyl) | $CH_3$ | $CH_3$ | 132–134 |
| 44 | $CH_3$ | S | H | $CH_3$ | $CH_3$ | $CH_3$ | 173–175 |
| 45 | $CH_3$ | S | H | $CH_2Cl$ | $CH_3$ | $CH_3$ | 156–158 |
| 46 | $CH_3$ | S | H | $CH_2F$ | $CH_2F$ | $CH_2F$ | 105–107 |
| 47 | $CH_3$ | S | H | $CH_2Cl$ | $CH_2Cl$ | $CH_2Cl$ | 154–156 |
| 48 | $CH_3$ | S | H | 4-chlorophenyl | $CH_3$ | $CH_3$ | 126–128 |
| 49 | $CH_3$ | S | H | benzyl ($CH_2$-phenyl) | $CH_3$ | $CH_3$ | 145–146 |
| 50 | $CH_3$ | S | H | $CH_3$ | $-CH_2-CH_2-$ | | 182–184 |
| 51 | $CH_3$ | S | H | $CH_3$ | $-CH_2-CCl_2-$ | | 178–180 |
| 52 | $CH_3$ | S | H | $CH_3$ | $-(CH_2)_4-$ | | 124–126 |
| 53 | $CH_3$ | S | H | $CH_3$ | $-(CH_2)_5-$ | | 130–131 |
| 54 | $CH_3$ | S | H | $CH_3$ | $-(CH_2)_2-CH[CH(CH_3)_2]-(CH_2)_2-$ | | 172–174 |

TABLE 2-continued

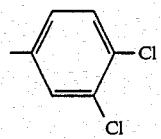

| Example No. | R¹ | X | R² | R³ | R⁴ | R⁵ | melting point/(°C.) |
|---|---|---|---|---|---|---|---|
| 55 | $CH_3$ | S | 3-Cl | $CH_3$ | $CH_3$ | $CH_3$ | 188–190 |
| 56 | $CH_3$ | S | 2-$CH_3$ | $CH_3$ | $CH_3$ | $CH_3$ | 130–131 |
| 57 | $CH_3$ | S | 2-$CH_3$ | $CH_3$ | —$(CH_2)_4$— | | 100–102 |
| 58 | $CH_3$ | S | H | $C_3H_7$ | $CH_3$ | $CH_3$ | 100–102 |
| 59 | $CH_3$ | S | H | $C_2H_5$ | $C_2H_5$ | $CH_3$ | 126–128 |
| 60 | H | S | H | $CH_3$ | $CH_3$ | $C_3H_7$ | 86–87 |
| 61 | H | S | H | $CH_3$ | —$(CH_2)_5$— | | 121–123 |
| 62 | H | S | 3-Cl | $CH_3$ | $CH_3$ | $CH_2Cl$ | 93–94 |
| 63 | H | S | 3-Cl | $CH_3$ | $CH_3$ | $CH_3$ | 124–125 |
| 64 | H | S | 2-$CH_3$ | $CH_3$ | $CH_3$ | $CH_3$ | 92–94 |
| 65 | H | S | 2-$CH_3$ | $CH_3$ | $CH_3$ | $CH_2Cl$ | 122–124 |
| 66 | $CH_3$ | O | H | $CH_3$ | $CH_3$ | 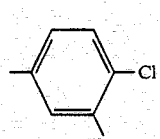 | 146–148 |
| 67 | $CH_3$ | O | H | H | —$(CH_2)_4$— | | 204–206 |
| 68 | $CH_3$ | S | H | $CH_3$ | F | F | 136–137 |
| 69 | $CH_3$ | S | H | $CH_3$ | $CH_3$ | 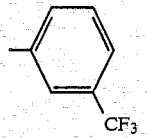 | 152–154 |
| 70 | $CH_3$ | S | H | $CH_3$ | $CH_3$ | 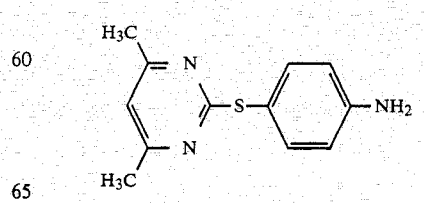 | 144–146 |
| 71 | $CH_3$ | S | H | H | —$(CH_2)_4$— | | 186–188 |
| 72 | $CF_3$ | S | H | $CH_3$ | $CH_3$ | $CH_3$ | 153–155 |
| 73 | $OCH_3$ | S | H | $CH_3$ | $CH_3$ | $CH_3$ | 184–186 |
| 74 | $SCH_3$ | S | H | $CH_3$ | $CH_3$ | $CH_3$ | 147–149 |

Preparation of starting substances

EXAMPLE 75

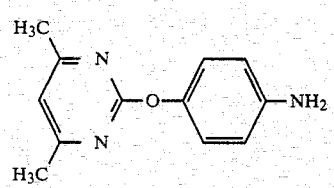 (II-1)

(Process d)

24.5 g (0.1 mole) of 2-(4-nitro-phenoxy)-4,6-dimethyl-pyrimidine were dissolved in 150 ml of dioxane and subjected to exhaustive hydrogenation with hydrogen in the presence of Raney nickel under a pressure of 50 bar at a temperature between 20° and 50° C. The catalyst was then filtered off with suction and the filtrate was evaporated under reduced pressure. 20.4 g (95% of theory) of 2-(4-amino-phenoxy)-4,6-dimethylpyrimidine were obtained in the form of a solid substance.

Melting point: 170°–171° C. (after recrystallisation from ethyl acetate).

The substances of the formula (II) listed in the following examples were also prepared by the method described in Example 75.

EXAMPLE 76

(II-2)

Melting point: 170°–172° C. (after recrystallisation from ethyl acetate)

EXAMPLE 77

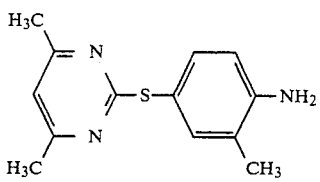
(II-3)

Melting point: 134°–135° C. (after recrystallisation from toluene).

EXAMPLE 78

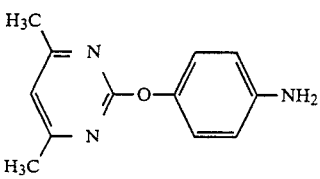
(II-1)

(Process c)

109 g (1 mole) of 4-amino-phenol were dissolved in 500 ml of dimethylsulphoxide. After addition of 56 g (1 mole) of powdered potassium hydroxide, the mixture was stirred at room temperature for 30 minutes and 143 g (1 mole) of 2-chloro-4,6-dimethyl-pyrimidine were then added in portions.

The mixture was warmed at 100° C. for 5 hours, cooled and then stirred into 3 liters of water. The crystals were filtered off with suction, washed several times with water and dried. 119 g (55.3% of theory) of 2-(4-amino-phenoxy)-4,6-dimethyl-pyrimidine were obtained.

Melting point: 170°–171° C. (after recrystallisation from ethanol).

The substances of the formula (II) listed in the following examples were also prepared by the method described in Example 78.

Example 79

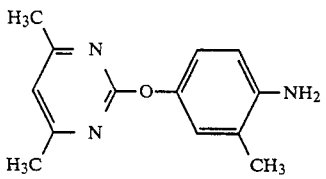
(II-4)

Melting point: 226°–228° C. (after recrystallisation from ethanol).

EXAMPLE 80

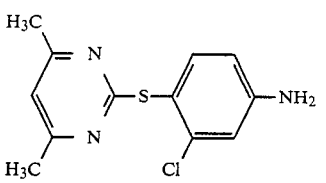
(II-5)

Melting point: 167°–168° C. (after recrystallisation from toluene)

EXAMPLE 81

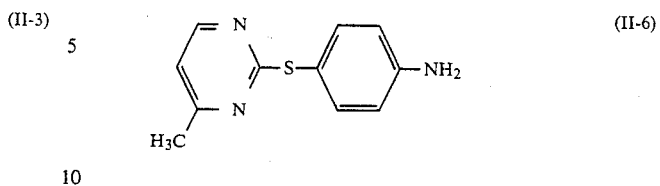
(II-6)

Melting point: 73°–74° C. (after recrystallisation from tetrachloromethan)

EXAMPLE 82

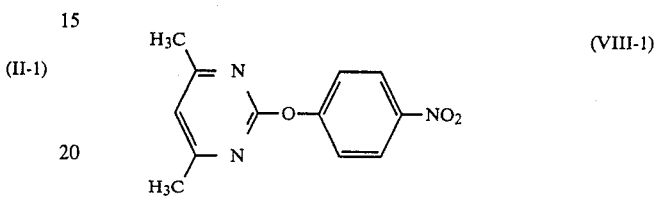
(VIII-1)

27.8 g (0.2 mole) of 4-nitro-phenol were dissolved in 100 ml of dimethylsulphoxide. After addition of 11.2 g (0.2 mole) of powdered potassium hydroxide, the mixture was stirred at room temperature for 30 minutes and 28.5 g (0.2 mole) of 2-chloro-4,6-dimethyl-pyrimidine were then added. The mixture was heated at 120° C. for 6 hours and then cooled, stirred with one liter of water and filtered off with suction. The crystals filtered off with suction were dried in air. 38 g (77.5% of theory) of 2-(4-nitrophenoxy)-4,6-dimethyl-pyrimidine were obtained.

Melting point: 108°–110° C.

Example 83

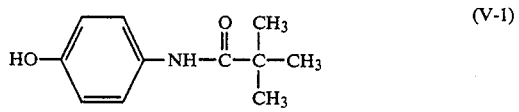
(V-1)

109 g (1 mole) of 4-amino-phenol and 101 g of triethylamine were dissolved in 700 ml of tetrahydrofuran. 120.5 g (1 mole) of pivalyl chloride were added dropwise at 10°–15° C., with stirring. The mixture was subsequently stirred at room temperature for 2 hours and then poured into 3 liters of water. The crystals precipitated were filtered off with suction and dried in air. 165 g (85.5% of theory) of 4-pivaloylamino-phenol were obtained.

Melting point: 168°–170° C.

The substances of the formula (V) listed in the following examples were also prepared by the method described in Example 83.

Example 84

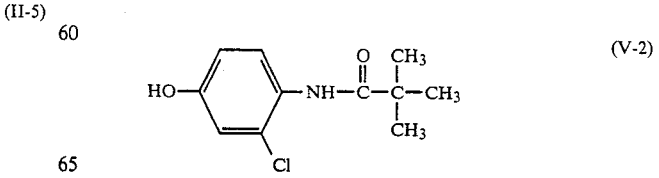
(V-2)

Melting point: 122°–124° C. (after recrystallisation from carbon tetrachloride).

Example 35

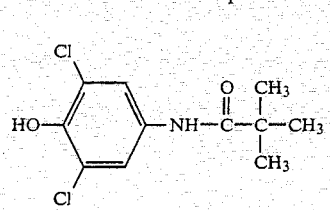

Melting point: 182°–184° C. (after recrystallisation with toluene)

EXAMPLE 86

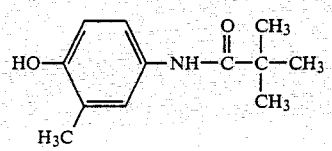

Melting point: 150°–152° C. (after recrystallisation with toluene)

Example 87

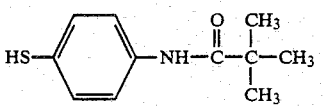

Melting point: 127°–128° C.

Use Example

The compound below was employed as a comparison substance in the following use example:

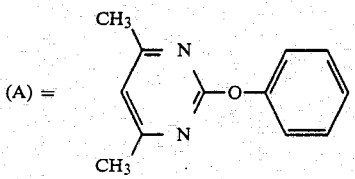

2-phenoxy-4,6-dimethyl-pyrimidine (known from U.S. Pat. No. 3,126,271).

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Tests plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the compound according to Example 45 shows a significantly better herbicidal activity than comparison substance (A) in the selective combating of Galinosoga, Galium, Sinapis, Stellaria, Echinochloa, Panicum and Poa in wheat and maize.

Example B

Critical concentration test/root-systemic action

Test insect: Myzus persicae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentation.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all the test animals have been killed and 0% if just as many tests insects are still alive as in the case of the untreated control.

In this test, for example, the compounds according to Examples (14), (20) and (38) are distinguished by a very good activity.

It will be understood that the specification and examples are illustrative, but not limitative of the present invention and that other embodiments within the spirit and scope of the invention will suggest themselves to those skilled in the art.

What is claimed is:

1. A substituted carboxylic acid anilide of the formula

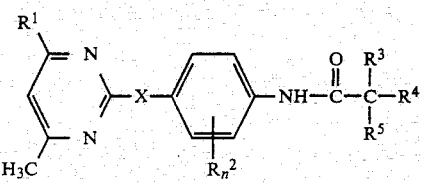

in which
X represents oxygen or sulphur,
$R^1$ represents hydrogen, halogen, alkyl with 1 to 6 carbon atoms, trifluoromethyl, phenyl, alkoxy with 1 to 6 carbon atoms, alkylmercapto with 1 to 6 carbon atoms, or phenyl substituted with chlorine, trifluoromethyl and/or methyl, $R^2$ represents halogen or methyl, n represents 0, 1 or 2, $R^3$ represents hydrogen, halogen, alkyl with 1 to 6 carbon atoms, alkyl with 1 to 6 carbon atoms, alkyl with 1 to 6 carbon atoms substituted with fluorine, chlorine and/or bromine, phenyl, benzyl, phenyl or benzyl each substituted with fluorine, chlorine, bromine, trifluoromethyl, methoxy and/or methyl, or the radicals —$OR^6$ or —$SO_m$—$R^6$, wherein $R^6$ represents alkyl with 1 to 6 carbon atoms, alkyl with 1 to 6 carbon atoms substituted by fluorine, chlorine and/or bromine, phenyl, or phenyl substituted by fluorine, chlorine, bromine and/or alkyl with 1 to 4 carbon atoms, and m represents 0, 1 or 2, and $R^4$ and $R^5$ independently of one another represent halogen, alkyl with 1 to 6 carbon atoms or alkyl with 1 to 6 carbon atoms substituted by fluorine, chlorine and/or bromine, or $R^4$ and $R^5$, together with the adjacent carbon atom, represent a carbocyclic ring with 3 to 8 ring carbon atoms optionally substituted by fluorine, chlorine and/or alkyl with 1 to 4 carbon atoms.

2. A compound as claimed in claim 1, wherein $R^1$ is hydrogen, fluorine, chlorine, bromine, alkyl with 1 to 4 carbon atoms, trifluoromethyl, phenyl or substituted phenyl, the substituents being selected from chlorine, trifluoromethyl and methyl, or is alkoxy with 1 to 4 carbon atoms or alkylmercapto with 1 to 4 carbon atoms.

3. A compound as claimed in claim 1, wherein $R^2$ is chlorine, bromine or methyl.

4. A compound as claimed in claim 1, wherein n is 0 or 1.

5. A compound as claimed in claim 1, wherein $R^3$ is hydrogen, fluorine, chlorine, bromine, alkyl with 1 to 4 carbon atoms, substituted alkyl with 1 to 4 carbon atoms, the substituents being selected from fluorine, chlorine and bromine, or is phenyl or substituted phenyl; the substituents being selected from fluorine, chlorine, bromine, trichloromethyl, methoxy and methyl, or is benzyl or substituted benzyl, the substituents being selected from fluorine, chlorine, bromine, trifluoromethyl, methoxy and methyl.

6. A compound as claimed in claim 1, wherein $R^3$ is a radical selected from —$OR^6$ and —$SO_mR^6$, in which $R^6$ is alkyl with 1 to 4 carbon atoms or substituted alkyl with 1 to 4 carbon atoms, the substituents being selected from fluorine, chlorine and bromine, or is phenyl or substituted phenyl, the substituents being selected from fluorine, chlorine, bromine and alkyl with 1 to 4 carbon atoms, and m is 0, 1 or 2.

7. A compound as claimed in claim 1 wherein $R^4$ and $R^5$ independently of one another are fluorine, chlorine, bromine, alkyl with 1 to 4 carbon atoms or substituted alkyl with 1 to 4 carbon atoms, the substituents being selected from fluorine, chlorine and bromine.

8. A compound as claimed in claim 1, wherein $R^4$ and $R^5$, together with the adjacent carbon atoms, are a saturated or unsaturated carbocyclic ring with 3 to 7 ring carbon atoms, or are a substituted saturated or unsaturated carbocyclic ring with 3 to 7 ring carbon atoms, the substituents being selected from fluorine, chlorine and alkyl with 1 to 4 carbon atoms.

9. A compound as claimed in claim 1, wherein X represents oxygen or sulphur, $R^1$ represents hydrogen, alkyl with 1 to 4 carbon atoms, alkoxy with 1 to 4 carbon atoms or trifluoromethyl, $R^2$ represents chlorine, bromine or methyl, n represents 0 or 1, $R^3$ represents fluorine, chlorine, bromine, alkyl which has 1 to 4 carbon atoms or substituted alkyl with 1 to 4 carbon atoms, the substituents being selected from fluorine and chlorine, or is phenyl or substituted phenyl, the substituents being selected from fluorine, chlorine and methyl, or is benzyl or substituted benzyl, the substituents being selected from fluorine, chlorine and methyl, or is a radical selected from —$OR^6$ and —$SO_mR^6$, in which $R^6$ is alkyl with 1 to 4 carbon atoms or substituted alkyl with 1 to 4 carbon atoms, the substituents being selected from fluorine and chlorine, or is phenyl or substituted phenyl, the substituents being selected from fluorine, chlorine and alkyl with 1 to 4 carbon atoms, and m is 0, 1 or 2, $R^4$ and $R^5$ independently of one another represent fluorine, chlorine, alkyl wth 1 to 4 carbon atoms or substituted alkyl with 1 to 4 ccarbon atoms, the substituents being selected from fluorine and chlorine, or $R^4$ and $R^5$, together with the adjacent carbon atom, represent a saturated or unsaturated carbocyclic ring with 3 to 7 ring carbon atoms, or represent a saturated or unsaturated substituted carbocyclic ring with 3 to 7 ring carbon atoms, the substituents being selected from fluorine, chlorine, methyl, ethyl, n-propyl, isopropyl, n-butyl, isobutyl, sec.-butyl and tert.-butyl.

10. A compound as claimed in claim 1, designated by the formula

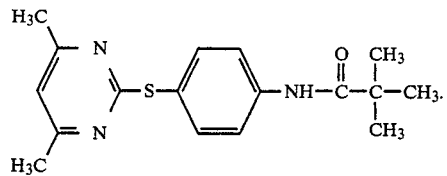

11. A compound as claimed in claim 1, designated by the formula

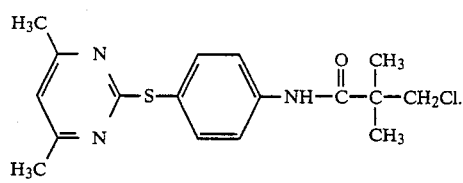

12. A compound as claimed in claim 1, designated by the formula

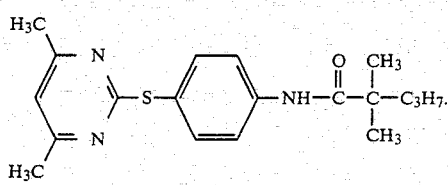

13. A compound as claimed in claim 1, designated by the formula

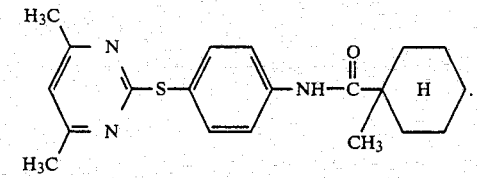

14. A compound as claimed in claim 1, designated by the formula

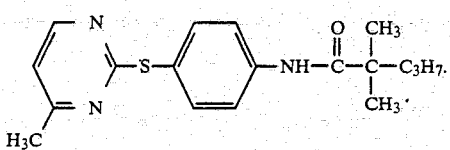

15. A herbicidal composition comprising an agriculturally acceptable carrier and, in herbicidally effective amount, a substituted carboxylic acid anilide as claimed in claim 1.

16. A herbicidal composition as claimed in claim 15, containing from 0.1 to 95% by weight of the active compound.

17. A method of combating weeds, which comprises applying to the weeds, or to their habitat, a herbicidally effective amount of a substituted carboxylic acid anilide as claimed in claim 1.

18. A method as claimed in claim 17, wherein the active compound is applied at a dosage of 0.01 to 10 kg per hectare.

19. A method as claimed in claim 17, wherein the active compound is a substituted carboxylic acid anilide selected from the compounds of the formulae:

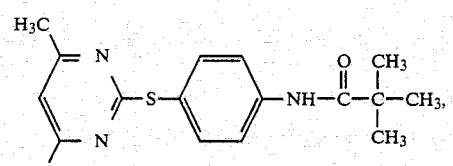

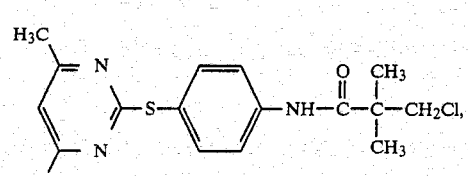

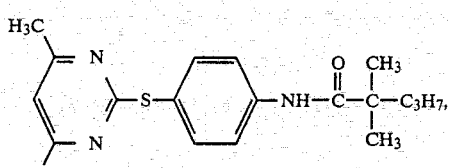

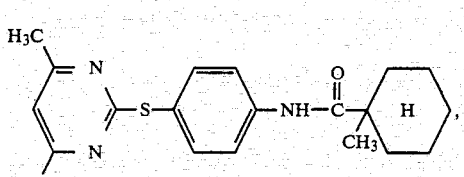

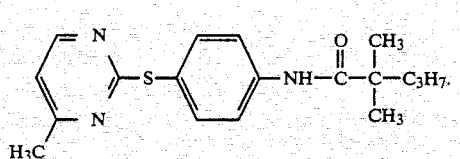

* * * * *